(12) United States Patent
Lee et al.

(10) Patent No.: US 9,119,550 B2
(45) Date of Patent: Sep. 1, 2015

(54) MAGNETIC RESONANCE AND ULTRASOUND PARAMETRIC IMAGE FUSION

(75) Inventors: Chi-Yin Lee, Sammamish, WA (US); Liexiang Fan, Sammamish, WA (US); Caroline Maleke, Bellevue, WA (US); Kevin Michael Sekins, Yarrow Point, WA (US); Patrick Gross, Langensendelbach (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 13/436,718

(22) Filed: Mar. 30, 2012

(65) Prior Publication Data

US 2013/0261429 A1    Oct. 3, 2013

(51) Int. Cl.
| | |
|---|---|
| *A61B 5/055* | (2006.01) |
| *A61B 8/00* | (2006.01) |
| *G01R 33/56* | (2006.01) |
| *A61B 5/00* | (2006.01) |
| *G01R 33/48* | (2006.01) |
| *G01R 33/563* | (2006.01) |
| *A61B 8/08* | (2006.01) |

(52) U.S. Cl.
CPC ............... *A61B 5/055* (2013.01); *A61B 5/0035* (2013.01); *A61B 5/7425* (2013.01); *A61B 8/4416* (2013.01); *A61B 8/485* (2013.01); *A61B 8/5261* (2013.01); *G01R 33/5608* (2013.01); *A61B 5/7207* (2013.01); *A61B 8/0891* (2013.01); *G01R 33/4804* (2013.01); *G01R 33/4814* (2013.01); *G01R 33/56358* (2013.01); *G01R 33/56366* (2013.01)

(58) Field of Classification Search
CPC .... A61B 5/055; A61B 5/7425; A61B 5/0035; A61B 5/7207; A61B 19/00; A61B 8/5261; A61B 8/4416; A61B 8/0891; A61B 8/485; G01R 33/5608; G01R 33/4814; G01R 33/56358; G01R 33/56366; G01R 33/4804
See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 6,508,768 B1 | 1/2003 | Hall et al. | |
| 6,558,324 B1 | 5/2003 | Von Behren et al. | |
| 8,363,066 B2* | 1/2013 | Weibrecht et al. | 345/629 |
| 2010/0008598 A1* | 1/2010 | Riley et al. | 382/299 |

(Continued)

OTHER PUBLICATIONS

Tang et al., "Multi-modal Imaging: Simultaneous MRI and Ultrasound Imaging for Carotid Arteries Visualization". Proceedings of the 29th Annual International Conference of the IEEE EMBS. Aug. 23-26, 2007. pp. 2603-2606.*
Wikipedia. "Least squares". revised Mar. 22, 2011. accessed Jan. 24, 2014 from <http://en.wikipedia.org/w/index.php?title=Least_squares&oldid=429896532>.*

(Continued)

*Primary Examiner* — Long V. Le
*Assistant Examiner* — Colin T Sakamoto

(57) ABSTRACT

Magnetic resonance and ultrasound parametric image is fused or combined. MRI and ultrasound imaging are used to acquire the same type of parametric images. Fused data is created by combining ultrasound and MRI parametric data at times for which both types of data are available. Rather than sacrificing rate, fused data is created for times for which MRI data is not acquired. A curve representing the values of the parameter over time is fit to the available MRI and ultrasound data of each location, resulting in fused data at times for which MRI data is not available.

10 Claims, 3 Drawing Sheets

(56) References Cited

U.S. PATENT DOCUMENTS

| | | |
|---|---|---|
| 2010/0254583 A1 | 10/2010 | Chan et al. |
| 2010/0290685 A1 | 11/2010 | Wein et al. |
| 2011/0060221 A1 | 3/2011 | Fan et al. |
| 2012/0195469 A1* | 8/2012 | Kirenko et al. ............... 382/103 |
| 2012/0207386 A1* | 8/2012 | Ofek et al. .................... 382/168 |

OTHER PUBLICATIONS

Wikipedia. "Image fusion". revised Mar. 19, 2011. accessed Jan. 24, 2014 from <http://en.wikipedia.org/w/index.php?title=Image_fusion&oldid=419672892>.*

Mullen et al., "MR, Ultrasound Fusion: Bridging the Gap between Clinical Benefits, Access and Equipment Utilization" SignaPULSE, spring 2009, a GE Healthcare MR Publication.*

* cited by examiner

MAGNETIC RESONANCE AND ULTRASOUND PARAMETRIC IMAGE FUSION

BACKGROUND

The present embodiments relate to multi-modality imaging. In particular, magnetic resonance imaging (MRI) and ultrasound imaging are combined.

Both MRI and ultrasound imaging generate images of anatomy. MRI has the benefits of generating clear and crisp images (e.g., higher signal-to-noise ratio) and is less affected by occlusion. However, the acquisition time for even anatomical MRI is slower than ultrasound imaging. Ultrasound imaging may provide real time imaging, even of a volume, at a higher rate. To combine data from both modalities, the rate of the ultrasound acquisition may be slowed, resulting in loss of temporal resolution. Combining images, even of the same anatomy at generally the same time, from the different modalities may be difficult due to speckle and other differences.

Both MRI and ultrasound imaging are capable of generating images other than anatomy, such as parametric images. Parametric images, such as elasticity, thermometry and perfusion images, provide additional diagnostic information compared to using only the traditional anatomical or flow images.

BRIEF SUMMARY

By way of introduction, the preferred embodiments described below include methods, systems, instructions, and computer readable media for magnetic resonance and ultrasound parametric image fusion. MRI and ultrasound imaging are used to acquire the same type of parametric images. Fused data is created by combining the most recent ultrasound and MRI data. The fused data may be created live or as acquired. Rather than sacrificing image rate, the ultrasound data is used to create fused data at times for which MRI data is not acquired. Curve fitting to the most recent ultrasound and MRI data is used to compute the fused data at high data rate.

In a first aspect, a method is provided for magnetic resonance and ultrasound parametric image fusion. Ultrasound parametric data representing a region of a patient is acquired at a first rate. The ultrasound parameter data are the first values of a parameter. The first values are derived from detected ultrasound data. Magnetic resonance parametric data representing the region of the patient are acquired at a second rate less than the first rate. The magnetic resonance parameter data is second values of the parameter. The second values are derived from magnetic resonance data. Fused values are calculated from the first and second values. The fused values represent the region of the patient at a third rate greater than or equal to the first rate. Fused parametric images are generated from the fused values.

In a second aspect, a non-transitory computer readable storage medium has stored therein data representing instructions executable by a programmed processor for magnetic resonance and ultrasound parametric image fusion. The storage medium includes instructions for computing parametric data for a sequence of images from both ultrasound data and magnetic resonance data, the parametric data at data rate equal to or higher than a rate of the ultrasound data, and outputting the sequence of the images, the images being a function of the parametric data.

In a third aspect, a system is provided for magnetic resonance and ultrasound parametric image fusion. A magnetic resonance (MR) system is configured to provide a first sequence of frames or volumes of MR data of an elastic characteristic, temperature characteristic, perfusion characteristic, or combinations thereof. An ultrasound system is configured to provide a second sequence of frames or volumes of ultrasound data of the elastic characteristic, temperature characteristic, perfusion characteristic, or combinations thereof. A processor is configured to combine the ultrasound data with the MR data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

High frame rate parametric images are generated from both magnetic resonance (MR) and ultrasound data. By combining low frame rate MR and high frame rate ultrasound data, parametric images combined from both modes are presented at a rate equal to or greater than the ultrasound acquisition. The combination of parametric images from MR and Ultrasound may provide good signal-to-noise images with high frame rate/volume rate.

Figure 1:
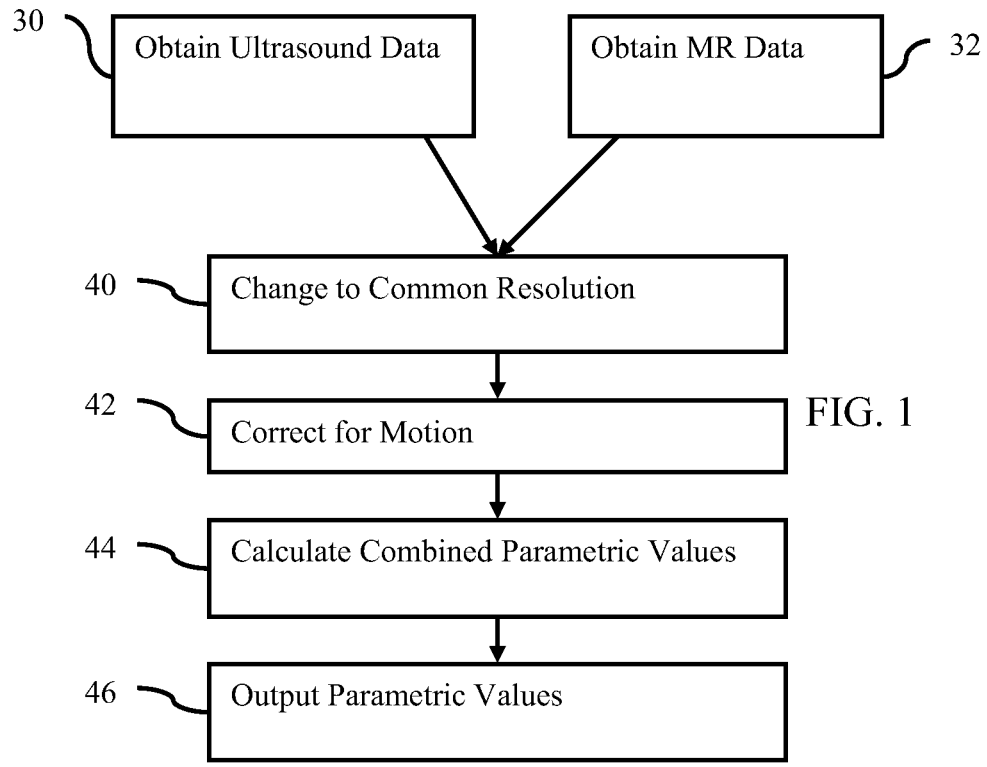
FIG. 1 is a flow chart diagram of one embodiment of a method for magnetic resonance and ultrasound parametric image fusion.

FIG. 1 shows a method for magnetic resonance and ultrasound parametric image fusion. The method is implemented by the system 10 of FIG. 3 or another system. The acts are performed in the order shown or other orders. For example, acts 30 and 32 are performed in an interleaved manner, sequentially, or at a same time. For sequential performance, an additional act of synchronizing the acquisitions with a cycle, such as heart or breathing cycle, may be performed. Acts 40-46 are performed in real-time with the acquisitions of acts 30 and 32, such as being performed in a same examination session, while acquisition or scanning is occurring, and/or within seconds of having scanned.

Additional, different, or fewer acts may be provided. For example, the change resolution act 40 and/or the correction for motion act 42 are not provided. As another example, act 46 is not provided. In another example, an act for temporally aligning MR and ultrasound data acquired at different times but a same or similar phase of a heart, breathing, or other cycle is provided.

The acquisitions of acts 30 and 32 are performed by ultrasound and MRI systems. The data is obtained in real-time or during the scans. Alternatively, the data was previously acquired and is obtained by data transfer or access to memory.

In act 30, ultrasound parametric data is acquired. Ultrasound data is acquired by acoustically scanning the patient in two or three dimensions. Any type of scan, scan format, or imaging mode may be used. For example, harmonic imaging is used with or without added contrast agents. As another example, B-mode, color flow mode, spectral Doppler mode, M-mode, contrast, or other imaging mode is used.

Ultrasound data representing anatomical or flow information is acquired from the patient by scanning. The data represents a point, a line, an area, or a volume of the patient. For ultrasound imaging, waveforms at ultrasound frequencies are transmitted, and echoes are received. The acoustic echoes are converted into electrical signals and beamformed to represent sampled locations within a region of the patient. The beamformed data may be filtered or otherwise processed, such as isolating information a harmonic or fundamental frequency band. Echoes at one or more harmonics of the transmitted waveforms may be processed.

The beamformed data may be detected, such as determining intensity (B-mode) or velocity (flow mode). A sequence of echo signals from a same location may be used to estimate velocity, variance, and/or energy. A sequence may also be used for detecting contrast agents. For example, the response to transmissions with different phases and/or amplitudes is added to isolate information from contrast agents as opposed to tissue or flow. Contrast agent detection may be used for perfusion. Other detection techniques from the beamformed data may be used. The detected ultrasound information is anatomical data. For example, B-mode data represents tissue structures. As another example, flow data indicates locations associated with a vessel. In yet another example, contrast agent data indicates contrast agents within the patient.

The detected values may be filtered and/or scan converted to a display format. The ultrasound data representing the patient is from any point along the ultrasound processing path, such as channel data prior to beamformation, radio frequency or in-phase and quadrature data prior to detection, detected data, or scan converted data.

Parameters may be derived from the ultrasound data. Parametric ultrasound data represents a characteristic of the patient or scan region rather than being a mere detected response of anatomy. Example parameters include temperature, elasticity, and perfusion. Other parameters may be used. For example, the types of tissue at different locations are determined from a speckle characteristic, echo intensity, template matching with tissue structure, or other processing.

The temperature parameter is derived from the ultrasound data with or without other information. By performing thermometry, the temperature of various locations may be determined. Any temperature-related or thermometry measurement may be used. For example, tissue expands when heated. Measuring the expansion may indicate temperature. Temperature related measurements may directly or indirectly indicate a temperature. For example, a measure of a parameter related to conductivity or water content (e.g., a measurement of the type of tissue) may indirectly impact the temperature. In one embodiment, two or more, such as all four, of tissue displacement, speed of sound, backscatter intensity, and a normalized correlation coefficient of received signals are performed. Other measurements are possible, such as expansion of vessel walls.

Tissue displacement is measured by determining an offset in one, two, or three-dimensions. A displacement associated with a minimum sum of absolute differences or highest correlation is determined. The current scan data is translated, rotated, and/or scaled relative to a reference dataset, such as a previous or initial scan. The offset associated with a greatest or sufficient similarity is determined as the displacement. B-mode or harmonic mode data is used, but other data may be used. The displacement calculated for one location may be used to refine the search or search region in another location. Other measures of displacement may be used.

The speed of sound may be measured by comparison from prior to heating with during heating. A pulse is transmitted. The time for the echo to return from a given location may be used to determine the speed of sound from the transducer to the location and back. Any aperture may be used, such as separately measuring for the same locations with different apertures and averaging. In another embodiment, signals are correlated. For example, in-phase and quadrature signals after beamformation are correlated with reference signals. A phase offset between the reference and current signals is determined. The frequency of the transmitted waveform (i.e., ultrasound frequency) is used to convert the phase difference to a time or speed of sound. Other measurements of the speed of sound may be used.

The backscatter intensity is B-mode or M-mode. The intensity or energy of the envelope of the echo signal is determined.

The normalized correlation coefficient of received signals may be measured. Beamformed data prior to detection, such as in-phase and quadrature data, is cross-correlated. In one embodiment, a reference sample or samples are acquired. During or after transmission of the sample, subsequent samples are acquired. For each location, a spatial window, such as three wavelengths in depth, defines the data for correlation. The window defines a length, area or volume. The current data is correlated with the reference data within the window space. The normalized cross-correlation is performed for the data in the window. As new data is acquired, further cross-correlation is performed.

Any temperature associated acoustic and physical parameters or changes in the parameters may be measured. Other measurements for thermometry may include tissue elasticity, strain, strain rate, motion (e.g., displacement or color flow measurement), or reflected power (e.g., backscatter cross-section).

In one embodiment, the temperature is estimated from a model rather than directly measured, such as disclosed in U.S. Patent Application No. 2011/0060221, the disclosure of which is incorporated herein by reference. One or more of the types of information discussed above may be used as inputs to the model. The actual data and/or derived information are anatomical parameters to be used in combination with the model. In addition to the ultrasound scanning, clinical or other information may be acquired for determining the temperature. For example, genetic information or other tissue related data may be mined from a patient record. Any feature contributing to determination of temperature related information may be used.

The temperature related measurements are applied to the model. Alternatively, the values (i.e., measurements and/or data) are processed and the processed values are input. For example, the values are filtered spatially and/or temporally. As another example, a different type of value may be calculated from the values, such as determining a variance, a derivative, normalized, or other function from the values. In another example, the change between the current values and reference or previous values is determined. A time-history of the values over a window of time may be used. The values are input as features of the model.

The model outputs a temperature or temperature distribution (i.e., temperature at different locations and/or times) from the input information. The derived temperature may be in any unit, such as degrees Fahrenheit or Celsius. The resolution of the temperature may be at any level, such as outputting temperature as being in one of multiple two or other degree ranges. Alternatively, other temperature related information is output, such as a change in temperature, a dose, or an index value.

Any model may be used, such as a neural network or a piecewise linear model. As an alternative to machine learning, manually programmed models may be used. In one embodiment, a thermal distribution model is used. The thermal distribution model accounts for the thermal conductivity, density, or other behavior of different tissues, fluids, or structures. The thermal distribution model determines the temperature at other locations. The thermal distribution model may determine the temperature at other times or both time and location.

Another parameter is elasticity. Any elasticity imaging may be used, such as strain or strain rate. Characteristics of the strain or elasticity may be used as the parameter. Acoustic energy, a thumper, cardiac motion, or other sources may be provided as a stress to cause displacement for measuring elasticity.

For strain or elasticity, the displacement of tissue is determined as a function of time. The displacement may be measured from tissue data, such as B-mode ultrasound data. Correlation, cross-correlation, minimum sum of absolute differences or other similarity measure is used to determine the displacement between scans. The displacements are determined along one, two, or three dimensions. In one embodiment, any one or more of the methods or systems disclosed in U.S. Pat. No. 5,107,837; 5,293,870; 5,178,147; 6,508,768 or 6,558,324, the disclosures of which are incorporated herein by reference, are used to generate elasticity frames of data or images as the strain information. Other methods of measuring strain or elasticity may be used. The displacement may be measured by determining tissue velocity and/or acceleration.

Based on one (e.g., velocity), two (B-mode correlation), or more (e.g., average displacement) scans, a strain field is determined. The strain field represents strain at the different locations. A displacement field or a strain rate field may be used in other embodiments. Other measurements may be used to represent strain or displacement, such as velocity.

In one embodiment, shear waves are detected in addition to or as an alternative to longitudinal waves. The excitation forms a beam, which generates a shear wave at spatial locations. Where the beam is sufficiently strong, a shear wave is generated. The shear wave propagates through tissue more slowly than the longitudinal wave along the acoustic wave emission direction. The shear wave propagates various directions, including a direction perpendicular to the direction of the applied stress. The displacement of the shear waves is greater at locations corresponding to the excitation beam. As the shear wave propagates through the scan lines, the B-mode intensity may vary. For the monitored scan lines, a sequence of data is provided representing a time profile of tissue motion resulting from the shear wave. For example, data from a plurality of spatial locations (e.g., along the scan lines) is correlated as a function of time. For each depth or spatial location, a correlation over a plurality of depths or spatial locations (e.g., kernel of 64 depths with the center depth being the point for which the profile is calculated) is performed. Two or three-dimensional displacement in space may be used. One-dimensional displacement along a direction different than the scan lines or beams may be used. The spatial offset with the highest or sufficient correlation at a given time indicates the amount of displacement. Displacements are determined for a given location at different times. The temporal profile for a given location indicates detection of the shear or longitudinal wave.

Velocity and/or modulus or other complex representation of elasticity may be used. The shear velocity and/or modulus may be determined, at least in part, based on the pressure and an absorption coefficient. The absorption coefficient may be assumed (e.g., 0.5, 0.6, 0.8 or other value) depending on the tissue being treated. The pressure applied is known from the transmitted excitation and consideration of attenuation.

Another parameter is perfusion. The concentration, rate, in-flow, out-flow, or other perfusion characteristic is derived from ultrasound data. The patient is scanned a plurality of times. In one embodiment, the scanning for detecting contrast agents is interleaved with scanning for destruction of contrast agents.

Perfusion is detected from the detected contrast agents. Any contrast agent detection scan mode may be used, such as harmonic B-mode. In one embodiment, multiple pulse techniques are used. Two or more transmissions along the same or adjacent transmit scan lines are fired. For example, two pulses, such as two opposite phase pulses, are used to isolate response at even harmonics. Contrast agents may have a stronger response than tissue at even harmonics. In addition or alternative to different phases and/or amplitudes for transmitted pulses, different weights of the receive signals may be used. In another example, three or more receive signals representing a same location are combined to determine the nonlinear fundamental response at the location. The corresponding transmit pulses have different phases and amplitudes. Nonlinear fundamental response is greater for contrast agents than tissue, so provides good specificity. The reperfusion is detected using combinations of multiple pulses. The contrast agents in the tissue of the region of interest at a given scan time are detected, indicating reperfusion at that time past the destruction or other introduction of contrast agents to the region.

Where contrast agents were destroyed, the perfusion detection is reperfusion. After transmission of the destructive acoustic energy, reperfusion of contrast agents is detected. The reperfusion is imaged using any technique, such as a contrast agent mode. In principle, the contrast agent concentration increases more rapidly in regions with high perfusion rates. The perfusion is detected over time.

The perfusion is derived from the contrast agent response. The amount of perfusion for a given location relative to the tissue may be determined. The contrast agent response alone may indicate perfusion concentration. Change in perfusion may be used. For a given location or voxel, the difference in contrast agent response between two times may be determined. The difference in amount of contrast agent response divided by the time separating the scans for the data indicates a perfusion rate.

The parametric information represents a region of the patient at a given time. The parametric data may be a temporal average. The region of the patient is two or three dimensional. Different or the same values are provided for different locations.

The parameter acquisition is repeated at different times. The scanning of the region, detection of ultrasound data from the scanning, and derivation of parameter values are repeated. The repetition provides parametric data representing the region at different times.

Any rate of repetition may be used. For example, one frame or volume of data representing the region is acquired each second. As another example, the rate is ten or more frames or volumes a second.

Any number of frames or volumes of the parametric ultrasound data are acquired. For example, three or more sets of parametric data are acquired, such as at first, second and third times. FIG. 2 shows acquisition of parametric ultrasound data (U) at seven different times. The acquisition may be ongoing. A time sequence of parametric data, such as thermometry, elasticity or perfusion, is acquired from the ultrasound scanner. For example, a plurality of temperature maps is obtained.

In act 32, magnetic resonance (MR) parametric data is acquired. The acquisition uses a MRI system, so may be performed at a same time as the acquisition of ultrasound data. Alternatively, the MR parametric data is acquired before, after, or interleaved with the ultrasound data. The MRI system and the ultrasound system are independent of each other. Alternatively, a combined system is provided, such as a transducer being mounted to a patient bed of the MRI system. Control, electronics, or processing may be shared or separate.

The MR parametric data is derived from MR data. For magnetic resonance, the received MR data indicates projection intensities. Using tomography or other processing, the intensity of response from different locations is determined. Different pulse sequences may be used to detect different molecules and/or characteristics at the scan region.

MR anatomy data may be obtained. The MR anatomy data represents anatomy of the patient. The MR anatomy data represents a volume of the patient, such as representing voxels in an N×M×O arrangement. Alternatively, the MR anatomy data represents a plurality of separate slices (e.g., three parallel slices). In other embodiments, the MR anatomy data represents a single plane.

One or more transmitters produce an RF excitation field. A desired number of the transmitters are employed and connected through a corresponding number of transmit/receive switches to a corresponding number of coils in an RF coil array. The combined RF fields of the coil elements produce a prescribed $B_1$ field throughout the region of interest in the subject. The signal produced by the subject in response to the RF excitation field is picked up by the coil array and applied to the inputs of the set of receive channels. The received signal is at or around the Larmor frequency. When the $B_1$ field is not being produced, the transmit/receive switches connect each of the receive channels to the respective coil elements. Signals produced by the excited spins in the subject are picked up and separately processed as k-space and/or object space data.

Any MR procedure for acquiring data representing the parameter, such as temperature, elasticity, or perfusion characteristics, may be used. For example, T1-weighted or T2-weighted data is obtained. As another example, diffusion data is obtained. For MR elastography data, any MR elastography process may be used. In one embodiment, the propagation of a mechanical wave is measured. The mechanical wave is induced in the patient by external pressure, such as cyclical pressure applied to the skin of the patient. For example, a pad (i.e., thumper) is placed on the abdomen of the patient and vibrates at a specific, low frequency. The frequency is low compared to the rate of scanning the region of interest by the MR system. In one embodiment, acoustic energy is used to generate the mechanical wave at a focal region within the patient. The mechanical wave moves through stiff and supple tissue at different rates.

To measure the propagation of the mechanical wave, MR scans are performed at different times. The reaction of the tissue to the mechanical wave is measured. The displacement of the tissue caused by the mechanical wave over time, time of travel, and distance indicate a velocity of the mechanical wave through the tissue. A processor determines the stiffness of the tissue based on the characteristic of the displacement. For example, the velocity of the mechanical wave is calculated for each of a plurality of sample locations. The velocity itself is used as the elastography data. Alternatively, peak normalized displacement or a parameter calculated from the velocity and/or peak normalized displacement is used as the MR elastography data. For example, stiffness or strain rate information is used.

In one embodiment, a phase—contrast MR technique using synchronous motion—sensitizing gradients measures the pattern of wave propagation. The resulting data is analyzed to generate quantitative MR elastography data of the stiffness or other mechanical properties of tissue. For example, harmonic low frequency transverse acoustic waves (10 Hz-1.1 kHz) are used as the source of external mechanical stress. The acoustic waves cause tiny cyclic displacements (on the order of tenths of microns). With mechanical waves (e.g., acoustic shear waves), the calculation of regional elastic modulus is simplified, because regional elastic modulus is computed directly from the local wavelength, rather than requiring estimation of the regional static stress distribution. A sensitive MR-based method scans to acquire information about the mechanical waves in tissue. An oscillating, motion sensitizing field gradient is applied synchronously with acoustic mechanical waves that are generated inside the imaged object. The cyclic motion of the spins in the presence of these motion-sensitizing gradients causes a measurable phase shift in the received MR signal. The phase shift is proportional to the displacement amplitude and the number of the cyclic motion-sensitizing gradients. Small amplitude synchronous motion may be measured by accumulating phase shifts over multiple cycles of mechanical excitation and the motion-sensitizing gradient waveform. From the measured phase shift in each voxel, the amplitude of displacement of each voxel is estimated in the reconstructed data. This displacement map shows the mechanical waves propagating within the object. The cyclic motion-sensitizing gradients may be superimposed along any desired axis, and therefore different components of the strain dyadic may be estimated non-invasively. Shear modulus images may be generated using spatial filtering to calculate local wavelength. The local wavelength, displacement, strain, or information derived there from is used as the elastography data.

Another MR parametric data parameter is temperature. Any MR thermometry technique may be used. For example, in T1-weighted imaging, the change in T1 longitudinal relaxation time of tissue can be used to image temperature changes. The T1 indicates the time required for tissue to become (re)-magnetized following a radio-frequency pulse. It is determined by thermal interactions between resonating protons and other nuclei. The proton resonance frequency (PRF) of water molecules shift with frequency, allows a change in frequency to be detected. The hydrogen electrons shield the nucleus from the magnetic field, effectively lowering the field seen by the nucleus and therefore the resonance frequency. In bonded electrons, this effect is reduced. With an increase in temperature, more bonds are stretched, broken or bent. This leads to a decreasing frequency with an increase in temperature.

Yet another parameter is perfusion. Any method may be used to determine diffusion using MRI. For example, the effect of gadolinium on the T2*relaxation time is used. The contrast agent locally destroys the magnetic field homogeneity. As a result, hydrogen nuclei within an imaging voxel will see different local magnetic fields and resonate at different frequencies. This in turn results in a loss of coherence of their signals. Their signals start to cancel. In an image, a reduction of the signal from a voxel (T2*shortening) depending on the amount of gadolinium contrast agent present results.

The perfusion parameter is calculated from the detected contrast agents. The concentration of the contrast agents may be used to represent perfusion. The change in contrast agents, in-flow, out-flow or other perfusion characteristic may be calculated.

The MR parameters are values for different locations of the region of the patient. The region is of the same two or three-dimensional locations as for the ultrasound parametric data. Alternatively, the region represented by the MR parametric data overlaps with but is not identical to the region represented by the parametric ultrasound data. The ultrasound and/or MR parametric data may be converted to a same coordinate system, such as using data registration, fiducial-based transformation, or position sensors.

The MR parametric data for an area or volume is acquired for a given time. The acquisition may be associated with a period. This period is treated as acquisition at a time. The data for a given time may represent instantaneous measurement or a temporal average. Parametric data representing the region at one time may be calculated from data also used to calculate the data for another time, such as in a moving window of data.

The MR parametric data is acquired multiple times. Any rate of acquisition may be used. The rate for the MR parametric data is less than the rate for the ultrasound parametric data. The ultrasound image sequence is at a higher frame or volume rate compared to the MRI image sequence. In the example of FIG. 2, one frame or volume of MR parametric data (M) is acquired for every three frames or volumes of ultrasound parametric data (U). The MR parametric data (M) is acquired every third time and not acquired at other times (e.g., not acquired at times two and three ($t_2$ and $t_3$)). Other differences in rate may be provided.

The time axis may be generalized, such as each time representing a period. While the MR parametric data and the ultrasound parametric data do not represent the identical time, both may represent the patient region in a range of time. Any size range may be used, such as 2, 1, 0.1, 0.01, or 0.5 seconds.

The times for each frame or volume of data may be relative to a trigger event (e.g., contrast agent destruction) or cycle. For example, the ultrasound parametric data of one frame or volume may represent the patient at an R-wave of the heart cycle and be acquired at 1:23:45 pm. The MR parametric data of one frame may represent the patient at the R-wave also, but be acquired at 5:43:21 pm. Both may be assigned time $t_1$ as the data represents the same time relative to the heart cycle. Alternatively, both types of data may be acquired at the same or similar (e.g., with a same period) absolute time. A timestamp of acquisition for each frame or volume is used to align the MR parametric data with the ultrasound parametric data in the time domain.

In act 40, the MR and ultrasound parametric data are changed to a common resolution. The spatial resolution for the MR and ultrasound parametric data may be different. For example, the spatial distribution of locations within the region of the patient represented by the different types of data is different. Interpolation, extrapolation, filtering, decimation, down-sampling, up-sampling, or other conversion is provided. The MR parametric data is converted to the resolution or sample grid of the ultrasound parametric data, or vice versa. Both types of data may be converted to a third resolution of sample grid.

In act 42, the sequences of MR and/or ultrasound data are corrected for motion. The correction aligns locations represented by data over time. Where motion causes a location to shift relative to the scanning, the locations may be aligned by motion compensation.

A motion estimation algorithm is used to generate motion compensated ultrasound parametric data. The same motion parameter is applied to the MR parametric data. The motion offset (e.g., rotation, translation, and/or scale) found for ultrasound for the relevant time is applied to the MR parametric data. Alternatively, the motion estimation is applied to the MR parametric data and the same motion parameters, after temporal interpolation, are applied to the ultrasound parametric data. In yet other embodiments, the MR parametric data and ultrasound parametric data are separately motion compensated.

The motion correction is applied to the parametric data. The estimation of motion to determine the correction uses anatomy data. The anatomy data used to derive the parametric data or anatomy data acquired during the scanning for the parametric data is used for motion compensation. Motion estimation may operate more accurately with anatomy features. Alternatively, the motion estimation is performed with the parametric data or both parametric and anatomy data.

Any registration may be used for motion compensation. The registration is rigid or non-rigid. Local cross-correlation (LCC) cost function, minimum sum of absolute differences, or other measure of similarity is used for motion estimation. The frames or volumes of the sequence are compared for different possible motion. Different translations and/or rotations are tested. For each test, a level of similarity is calculated. The transition and rotation combination with the greatest level of similarity indicates the motion between the frames or volumes of data. Any search pattern may be used, such as numerical optimization, course-to-fine searching, subset based searching, or use of decimated data. Scaling may be used in addition to translation and rotation.

Motion is estimated between all of the frames and volumes relative to one, a reference. Alternatively, the registration is performed along the sequence between temporally adjacent frames or volumes.

The registration is along two or three-dimensions. Any combination of translation and rotation degrees of freedom may be used, such as 6 degrees (3 axes of rotation and 3 axes of translation). Scaling or non-rigid transforms may be used.

The correlation may be based on all of the data in the sets or sub-sampled data. The correlation may be for data or for features. For example, a plurality of features is identified by the user or automatically by a processor. The features are correlated between frames or volumes. The features may be tissue boundaries, tissue regions, bone region, fluid region, air region, combinations thereof, or other feature. The data representing the features with or without surrounding data is used for the correlation. The features may be identified in one set (e.g., ultrasound) for matching with all of the data in another set, or features of one set may be matched to features of another set.

Once the translations and rotations for the sequence are determined. The frames or volumes are shifted accordingly for calculating the fused, parametric values. The fused, parametric values may be determined from the shifted frames or volumes. Alternatively, the motion is used for selecting data from the different frames or volumes for calculating the fused, parametric values.

In act 44, fused, parametric values are calculated from the MR and ultrasound parameter data. Parametric values from ultrasound and MR are combined to form fused values. The values for the parameter are combined, such as combining temperatures from MR and ultrasound.

Any type of combination may be used, such as a weighted combination. Weighting allows more emphasis on one type of data than another, such as weighting MR parameters more heavily than ultrasound to increase signal-to-noise ratio.

The combination is of parameter values for a given location. For example, MR and ultrasound parameter data are provided for a 200×200 pixel field. For a given motion compensated location (x, y (e.g., x=50, y=123)), the parameter values for that location from the sequence are combined. The parameter values at location x, y over time for both MR and ultrasound are used to determine the fused, parametric values for that location. Spatial averaging or filtering may be used prior to the combination. The calculation of the fused values is repeated for different locations using the parametric data appropriate for that location.

The combination is of parametric values for different times. The fused, parametric data represents temporal sampling at a rate. The rate is the same or different from the rate of MR or ultrasound acquisition. The fused image data rate may be even higher than the ultrasound acquisition rate. If the fused image to be constructed is at a time which either Ultrasound data (FIG. 2a) or MR data is available (FIG. 2b), the fused image generation can be considered as a filtering process using the current and prior MR and ultrasound data inside the moving window along the time axis. If the fused image to be constructed is at a time which neither MR data nor ultrasound data (FIG. 2c) is available, the fused image generation can be considered as an extrapolation process using the prior MR and ultrasound data inside the moving window.

Figure 2A:
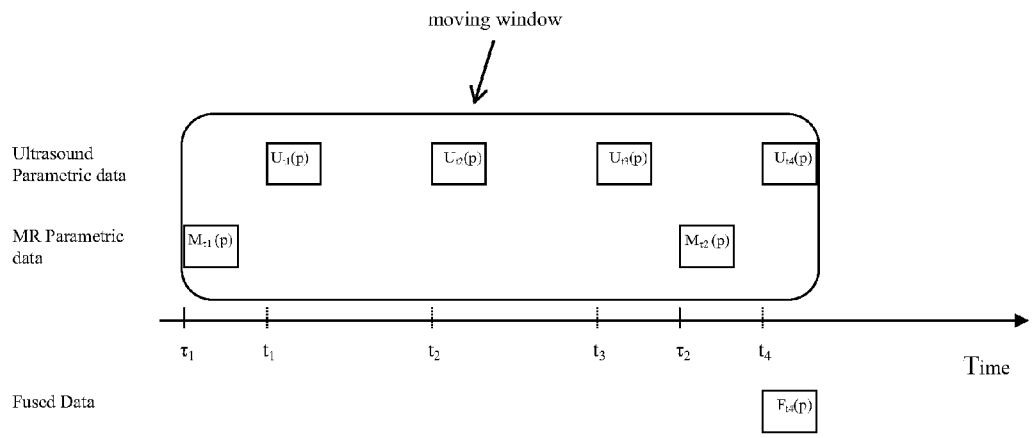
FIGS. 2A-C are illustrations of example rates for magnetic resonance, ultrasound, and fused data.
Figure 2B:
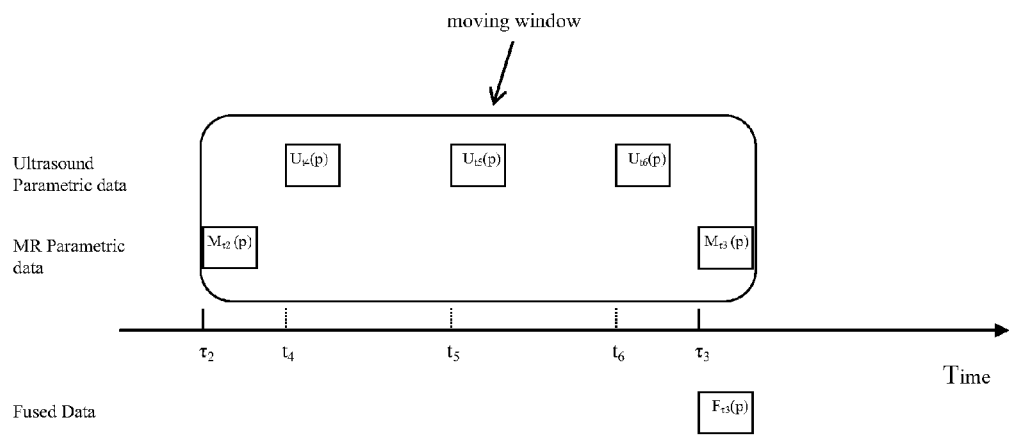
Figure 2C:
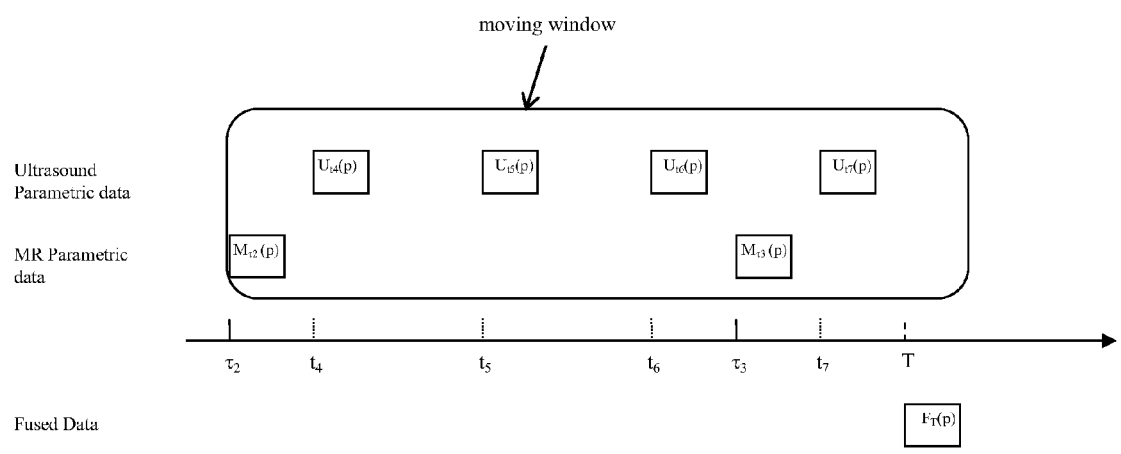

The filtering or extrapolation process for generating fused parametric images are performed by piecewise weighted least square quadratic curve fitting in a moving window. The size (time duration) of the moving window is chosen to be long enough to cover at least the two most recent MR parametric data points. FIGS. 2a, 2b and 2c are examples of the moving windows at points of time for generating the fused data. In another embodiment, the moving window with size is longer, such as long enough to cover the most recent three or more MR parametric data points.

In one embodiment, a weighted least square fitting of the MR and ultrasound parametric values is performed. Other fitting functions may be used. The parameter values from both ultrasound and MR are used in a same function to determine the fitted curve. Any curve may be fit, such as a piecewise quadratic function or high degree polynomial.

To fit the piecewise quadratic function, an energy function is minimized. The energy function includes the ultrasound and MR parametric values from a moving window. For the example in FIG. 2a, to compute the fused image value at time $t_4$, the moving window is formed and the energy function includes the parametric values from times $\tau_1$ to $t_4$. The fusion image value $f(t_4)$ at any point (x, y) is obtained by a weighted least square fitting curve using the parametric values. Consider quadratic curve $f(t)=at^2+bt+c$. Values a, b, and c may be obtained by minimizing the following energy function:

$$E_1 = w_U \underbrace{\sum_{i=1}^{4} [U_{t_i} - f(t_i)]^2}_{\text{Ultrasound parametric data}} + w_M \underbrace{\sum_{j=1}^{2} [M_{\tau_j} - f(\tau_j)]^2}_{\text{MR parametric Data}}$$

where $U_{t_i}$ is the ultrasound parametric value of point (x, y) at time $t_i$, $M_{\tau_j}$ is the MR parametric value of the point (x, y) at time $\tau_j$, and $w_U$ and $w_M$ are weighting coefficients for the ultrasound and MR parametric values, respectively. By minimization, a, b and c may be estimated and the fused, parametric value, f, at time $t_4$ may be computed.

The weights are assigned as desired. For example, the weights are equal. As another example, the weights for the MR parameter values are greater. Any relative weighting may be used. The weights set the relative contribution to the fitted curve from the particular type of data.

Using the fit curve in a moving window, a fused, parametric value may be computed. The moving window is updated at different locations or times and so is the fitting curve. Fused, parametric values are provided for all of the locations or times as required by the desired output data rate.

In act 46, a sequence of the images is output. Each image is a function of the fused, parametric data. The values for each location of each image in the sequence are provided by the respective fit curve. The locations are distributed in two or three-dimensions. The images represent the parameter for the region of the patient at different times. Any color or grayscale modulation or display technique for parametric imaging may be used. For example, each pixel represents a location. The pixel intensity and/or color are modulated by the fused, parametric value for that time and location.

The images are output for display, such as outputting to a display. Alternatively, the images are output to a database, such as outputting for later retrieval.

The weighted least square curve is used to generate high frame rate fused, parametric images. The sequence of fused images may be displayed at the rate associated with ultrasound acquisition or another rate, such as a real-time rate of twenty or more frames or volumes a second. The rate may be greater than the MR acquisition rate.

Separate images for the separate modalities may also be provided. The fused, parametric image may be overlaid as a color on a grayscale anatomy image. Graphical overlays or other information on or in the fused, parametric images may be presented to the user. The images are renderings from volume data or are planar representations of a plane. The plane may be a scan plane or may be a plane extracted from a scanned volume.

Figure 3:
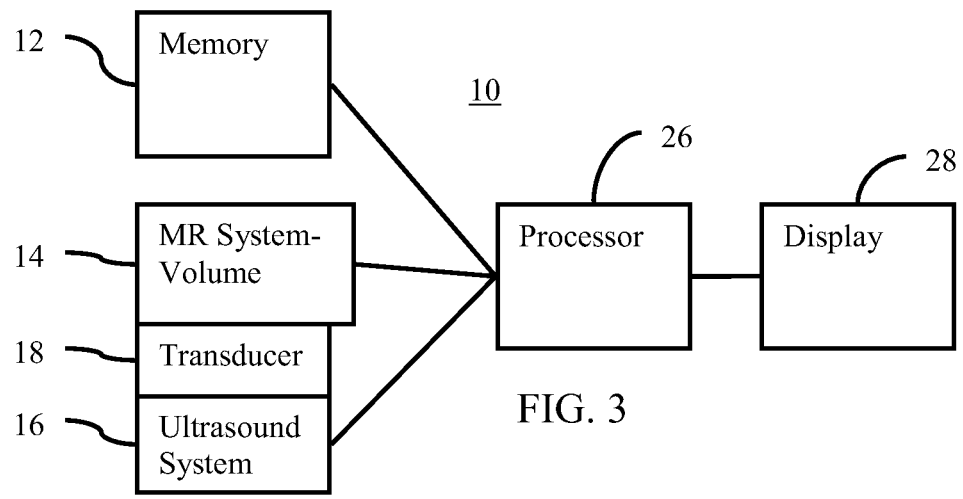
FIG. 3 is a block diagram of one embodiment of a system for magnetic resonance and ultrasound parametric image fusion.

FIG. 3 shows a system 10 for magnetic resonance and ultrasound parametric image fusion. The system 10 includes a memory 12, an MR system 14, an ultrasound system 16, a transducer 18, a processor 26, and a display 28. Additional, different, or fewer components may be provided. For example, a network or network connection is provided, such as for networking with a medical imaging network or data archival system. As another example, separate transducers 18 are used for acquiring MR elastography data and ultrasound data. In another example, a user interface is provided. The MR system 14, transducer 18, and ultrasound system 16 may not be provided in some embodiments, such as where the ultrasound and MR parametric data is acquired by transfer or from storage.

The processor 26 and display 28 are part of a medical imaging system, such as the diagnostic or therapy ultrasound system 16, MR system 14, or other system. Alternatively, the processor 26 and display 28 are part of an archival and/or image processing system, such as associated with a medical records database workstation or server. In other embodiments, the processor 26 and display 28 are a personal computer, such as desktop or laptop, a workstation, a server, a network, or combinations thereof.

The display 28 is a monitor, LCD, projector, plasma display, CRT, printer, or other now known or later developed devise for outputting visual information. The display 28 receives images, graphics, or other information from the processor 26, memory 12, MR system 14, or ultrasound system 16.

One or more images representing elasticity, thermometry, perfusion, combination thereof, or other parameters of a patient are displayed. At least some of the values for the parameters of the image are determined, at least in part, from both MR and ultrasound parameter values. For example, an image rendered from a three-dimensional data set of fused, parametric values is provided adjacent to an image from real-time ultrasound scanning and/or an image from MR anatomy scanning. Ultrasound or MR parametric images without fusion may also be displayed. Two-dimensional images presenting a planar region of the patient may be displayed. Any of the types of data may be combined to form an image or displayed separately at a substantially same time.

The magnetic resonance (MR) system 14 includes a cyromagnet, gradient coil, and body coil in an RF cabin, such as a room isolated by a Faraday cage. A tubular or laterally open examination subject bore encloses a field of view. A more open arrangement may be provided. A patient bed (e.g., a patient gurney or table) supports an examination subject, such as a patient with or without one or more local coils. The patient bed may be moved into the examination subject bore in order to generate images of the patient. Received signals may be transmitted by the local coil arrangement to the MR receiver via, for example, coaxial cable or radio link (e.g., via antennas) for localization.

Other parts of the MR system are provided within a same housing, within a same room (e.g., within the radio frequency cabin), within a same facility, or connected remotely. The other parts of the MR system may include local coils, cooling systems, pulse generation systems, image processing systems, and user interface systems. Any now known or later developed MR imaging system may be used. The location of the different components of the MR system 14 is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The MR system 14 is configured by software, hardware, or both to acquire data representing a plane or volume in the patient. In order to examine the patient, different magnetic fields are temporally and spatially coordinated with one another for application to the patient. The cyromagnet generates a strong static main magnetic field $B_0$ in the range of, for example, 0.2 Tesla to 3 Tesla or more. The main magnetic field $B_0$ is approximately homogeneous in the field of view.

The nuclear spins of atomic nuclei of the patient are excited via magnetic radio-frequency excitation pulses that are transmitted via a radio-frequency antenna, such as a whole body coil and/or a local coil. Radio-frequency excitation pulses are generated, for example, by a pulse generation unit controlled by a pulse sequence control unit. After being amplified using a radio-frequency amplifier, the radio-frequency excitation pulses are routed to the body coil and/or local coils. The body coil is a single-part or includes multiple coils. The signals are at a given frequency band. For example, the MR frequency for a 3 Tesla system is about 123 MHz+/−500 KHz. Different center frequencies and/or bandwidths may be used.

The gradient coils radiate magnetic gradient fields in the course of a measurement in order to produce selective layer excitation and for spatial encoding of the measurement signal. The gradient coils are controlled by a gradient coil control unit that, like the pulse generation unit, is connected to the pulse sequence control unit.

The signals emitted by the excited nuclear spins are received by the local coil and/or body coil. In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior), under (posterior), or in the patient. The received signals are amplified by associated radio-frequency preamplifiers, transmitted in analog or digitized form, and processed further and digitized by the MR receiver.

The recorded measured data is stored in digitized form as complex numeric values in a k-space matrix. A one or multi-dimensional Fourier transform reconstructs the object or patient space from the k-space matrix data.

The MR system 14 may be configured to acquire different types of data. For example, the MR data represents the anatomy of the patient. The MR data represents the response to the magnetic fields and radio-frequency pulses of tissue. Any tissue may be represented, such as soft tissue, bone, or blood.

The MR system 14 may be configured for acquiring specialized functional or anatomic information. For example, T1-weighted, diffusion, or T2-weighted MR data is acquired. In one embodiment, the MR system 14 is configured for acquiring elastography, thermometry, perfusion, or other parametric information. For MR elastography, the transducer 18 may apply acoustic radiation force focused at one or more locations in the patient. In response to phased summation of the acoustic energy from the elements of the transducer 18, the acoustic energy causes a longitudinal and/or shear wave to propagate from the focal region. The MR scan is used to measure displacement. The displacement amplitude may indicate an elastic characteristic of the tissue. Other MR elastography techniques may be used.

The MR system 14 scans the patient over time. A sequence of frames or volumes of MR data is acquired. The MR data is used to derive the parametric values for different locations in the area or volume. These MR parametric values may be associated with better signal-to-noise ratio, but less rapid volume or frame rate than the same parameter acquired using the ultrasound system 16.

The ultrasound system 16 is any now known or later developed ultrasound imaging system. For example, the ultrasound system 16 includes the transducer 18 for converting between acoustic and electrical energies. Transmit and receive beamformers relatively delay and apodize signals for different elements of the transducer 18. B-mode, Doppler, or other detection is performed on the beamformed signals. A scan converter, memory, three-dimensional imaging processor, and/or other components may be provided.

The transducer 18 is a one-, two-, or multi-dimensional array of piezoelectric or capacitive membrane elements. In one embodiment, the transducer 18 is a handheld or machine held transducer for positioning against and outside of the patient. In another embodiment, the transducer 18 is part of a probe for use within the patient, such as a transesophageal probe. For example, the transducer 18 is a one-dimensional array of elements within or on a catheter used for intervention or a different purpose. In yet another embodiment, the transducer is positioned in a patient bed of the MR system or by a robot for use on the patient while in the MR bore for scanning.

The ultrasound data is output in a polar coordinate or scan converted Cartesian coordinate format. Acoustic energy is used to scan a plane and/or volume. For example, a volume is scanned by sequentially scanning a plurality of adjacent planes. Any format or scan technique may be used. The scanned volume may intersect or include all of the patient volume. For example, the breast is scanned with ultrasound along one or more two-dimensional planes.

The ultrasound system 16 is configured to derive parametric values. For example, temperature, perfusion, elasticity, or other parameter characteristics are calculated. The parameter values are determined from detected data, such as detected tissue, flow, and/or contrast agents. The parameter values are derived for each of a sequence of frames or volumes. The frames or volumes have a rate in the sequence greater than the rate of MR parametric frames or volumes.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 12 is part of an imaging system, part of a computer associated with the processor 26, part of a database, part of another system, or a standalone device.

The memory 12 stores datasets (e.g., frames or volumes) each representing a three-dimensional patient volume or a two-dimensional patient plane. The patient volume or plane is a region of the patient, such as a region within the chest, abdomen, leg, head, arm, or combinations thereof. The patient volume is a region scanned by the MR system 14 and the ultrasound system 16.

Any type of data may be stored, such as medical image data (e.g., ultrasound and MR parametric and ultrasound anatomy data). The data represents the patient over time, such as prior to or during treatment or other procedure.

The stored data is interpolated or converted to an evenly spaced two or three-dimensional grid or is in a scan format. The data for different modalities may be transformed to be on a same grid or format. The data from different times may be altered to account of motion.

The memory 12 or other memory is a non-transitory computer readable storage medium storing data representing instructions executable by the programmed processor 26 for magnetic resonance and ultrasound parametric image fusion. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for fusing parametric information from multiple modalities. The processor 26 is a single device or multiple devices operating in serial, parallel, or separately. The processor 26 may be a main processor of a computer, such as a laptop or desktop computer, or may be a processor for handling tasks in a larger system, such as the MR or ultrasound systems 14, 16. The processor 26 is configured by software and/or hardware.

The processor 26 is configured to combine ultrasound and MR parametric information. The processor 26 receives the parametric information from the MR and ultrasound systems 14, 16. Alternatively, the processor 26 receives MR and ultrasound data and generates the ultrasound parametric data and the MR parametric data. The processor 26 may filter or otherwise process the parametric data prior to combination. For example, the processor 26 converts the data to a same format or resolution. As another example, the processor 26 corrects for motion through the sequences of data. The processor 26 may assemble the sequences, such as determining a temporal alignment of the ultrasound sequence relative to the MR sequence.

The processor 26 is configured to combine the ultrasound parametric data with the MR parametric data. Due to different scan or acquisition rates, the fused parametric data may be generated to a rate corresponding with the ultrasound data. In one embodiment, the processor uses a weighted least square fitting of the MR and ultrasound data from different times to filter or to extrapolate. Other filtering and extrapolation can be used.

The processor 26 outputs the combined parametric data. For example, temperature, elasticity, or perfusion data representing a plurality of locations in a plane or volume is output. The values for the data are based on both imaging modalities. The ultrasound data contributes temporal information, allowing for parametric images at a higher rate than MR alone. The MR data contributes signal-to-noise ratio, allowing for parametric images with more signal than ultrasound alone.

The output is data prior to conversion for display or is image data converted for display. For example, the data is RGB data for pixels on a display. As another example, the data represents a volume prior to rendering or represents a two-dimensional rendering of the volume.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for magnetic resonance and ultrasound parametric image fusion, the method comprising:

acquiring, by an ultrasound system, ultrasound parametric data representing different locations in a region of a patient at a first rate, the ultrasound parameter data comprising first values of a parameter of a characteristic of the patient, the first values calculated from B-mode detected ultrasound data or flow mode from estimated velocity, energy, or variance ultrasound data;

acquiring, by a magnetic resonance system, magnetic resonance parametric data representing the different locations in the region of the patient at a second rate less than the first rate, the magnetic resonance parameter data comprising second values of the parameter of the same characteristic of the patient, the second values derived from magnetic resonance data;

calculating, by a processor, fused values separately for each of the locations, the calculating for each of the locations using a respective curve fitted to the first and second values over time for the location, the fused values representing the region of the patient at a third rate greater than the second rate such that the second values of the parameter from the magnetic resonance parametric data representing the patient at a first time are used to calculate the fused values representing the patient at a second, different time for which the second values are not provided; and generating, on a display, fused, parametric images from the fused values.

2. The method of claim 1 wherein acquiring the ultrasound parametric data and the magnetic resonance parametric data comprises acquiring elasticity data, thermometry data, or perfusion of contrast agent data, the parameter comprising an elasticity characteristic, a temperature, or a perfusion of contrast agent characteristic.

3. The method of claim 1 wherein acquiring the ultrasound parametric data at the first rate and acquiring the magnetic resonance parametric data at the second rate comprise acquiring the ultrasound parametric data at a frame or volume rate faster than the acquiring of the magnetic resonance parametric data.

4. The method of claim 1 wherein calculating the fused value at a time $T_{high}$ comprises applying a moving window extending from a time $T_{low}$ ($T_{low} < T_{high}$) to the time $T_{high}$ where $T_{low}$ is a time at which a second to last frame of magnetic resonance parametric data was acquired, and calculating the fused value for a time range defined by the moving window.

5. The methods of claim 4 wherein calculating comprises minimizing an energy function of the first values and the second values in the moving window, the fit curve being used to generate the fused value at $T_{high}$.

6. The method of claim 1 wherein calculating comprises performing a weighted least square fitting of the first and second values in a moving window.

7. The method of claim 1 wherein calculating comprises calculating the fused values to represent the region at the first rate, the first and third rates being equal.

8. The method of claim 1 wherein generating the fused, parametric images comprises displaying a sequence of the fused, parametric images at the third rate, the fused, parametric images being of the parameter and of the region.

9. The method of claim 1 further comprising:
interpolating the first, second, or first and second values to a common resolution prior to calculating.

10. The method of claim 1 further comprising:
correcting spatial locations of the first, second, or first and second values for motion using magnetic resonance and ultrasound data representing anatomy.

\* \* \* \* \*

UNITED STATES PATENT AND TRADEMARK OFFICE
CERTIFICATE OF CORRECTION

PATENT NO. : 9,119,550 B2  
APPLICATION NO. : 13/436718  
DATED : September 1, 2015  
INVENTOR(S) : Chi-Yin Lee et al.

Page 1 of 1

It is certified that error appears in the above-identified patent and that said Letters Patent is hereby corrected as shown below:

ON THE TITLE PAGE

Item 73 "Siemens Aktiengesellschaft" with Residence in "Germany" should be named as an additional Assignee.

The correct Assignees are "Siemens Medical Solutions USA, Inc." with Residence in "Malvern, PA" and "Siemens Aktiengesellschaft" with Residence in "Germany".

Signed and Sealed this  
Eighth Day of March, 2016

Michelle K. Lee  
*Director of the United States Patent and Trademark Office*